US00PP12144P2

(12) United States Plant Patent
McColley

(10) Patent No.: US PP12,144 P2
(45) Date of Patent: Oct. 16, 2001

(54) PHILODENDRON PLANT NAMED 'MCCOLLEY'S FINALE'

(76) Inventor: Cora McColley, 1515 Pine Bluff Ave., Orlando, FL (US) 32806

( * ) Notice: Subject to any disclaimer, the term of this patent is extended or adjusted under 35 U.S.C. 154(b) by 0 days.

(21) Appl. No.: 09/310,950

(22) Filed: May 13, 1999

(51) Int. Cl.[7] ..... A01H 5/00
(52) U.S. Cl. ..... Plt./381
(58) Field of Search ..... Plt./381

(56) References Cited

U.S. PATENT DOCUMENTS

P.P. 3,831 3/1976 McColley ..... Plt./318
P.P. 5,355 11/1984 McColley ..... Plt./318
P.P. 6,797 5/1989 Miller ..... Plt./318

*Primary Examiner*—Bruce R. Campell
*Assistant Examiner*—Wendy Couchoud Baker
(74) *Attorney, Agent, or Firm*—Lawrence E. Laubscher, Jr.

(57) ABSTRACT

There is disclosed a stocky, compact self-heading Philodendron plant of unique color, having new leaves of rich chestnut red color, which color changes as the leaves mature, to a dark chestnut red and then to a medium green with dark chestnut red shading, dark chestnut red cataphylls and red black petioles add to the overall distinctive color of the plant, which retains its coloration in moderate indoor conditions.

2 Drawing Sheets

BACKGROUND OF THE INVENTION

My present invention is that of a new and distinct cultivar of Philodendron plant which is the result of hybridization of Philodendron plants of unknown complex hybrid parentage.

Since the 1960's, an extensive Philodendron hybridizing program has been carried out in the vicinity of Orlando, Fla. Originally conceived and conducted by my late husband, Robert H. McColley, the hybridization efforts were continued under my auspices for several years by Dr. Howard N. Miller. Following Dr. Miller's retirement several years ago, the hybridization program was largely discontinued. However, I continued to raise thousands of plants from numerous crosses previously made, with particular interest in self-heading Philodendron plants having distinctive foliage color. Among a batch of seedlings of unknown parentage I identified and isolated a single plant which was strikingly different from all known Philodendron varieties. The single plant was a self-heading, rather than vining, variety, with rich red coloration in its new leaves. I have asexually reproduced the new variety from crown offshoots at nursery facilities located in the vicinity of Orlando, Fla. The new variety retains its distinctive characteristics through successive generations of asexual reproduction by vegetative cuttings of crown offshoots. Because the plant is compact, self-heading and has little stem, it is not commercially practical to propagate the plant from vegetative cuttings. The plant can be mass produced by tissue culture propagation techniques (organogenesis, using meristematic explants), and has been found to retain its distinctive characteristics through successive generations of asexual reproduction.

SUMMARY OF THE INVENTION

My new variety can be readily distinguished from all other varieties of Philodendron by the combination of its self-heading growth habit, the shape of the leaves and the unique rich red coloration of new leaves.

My new variety has been grown under various conditions at several locations in the vicinity of Orlando, Fla., including Zellwood, Fla. and Apopka, Fla.. It maintains its form and color under a light range of 1,000–1,800 foot-candles and a temperature range of 60° F.–90° F., plus or minus 5° F. for brief periods. Occasional short term exposure to higher temperatures has no substantial adverse effect. Prolonged exposure to extreme high temperatures adversely affects growth. Prolonged exposure to intense sunlight is damaging to the plant, and exposure to very high light intensities may affect foliage coloration. The plant grows well under moderate indoor conditions and is suitable for interior plantscaping.

Because of its unique combinations of color, leaf shape and growth habit, Philodendron 'McColley's Finale' is distinctive from all other Philodendrons. While it shares some characteristics of certain other hybrids, it is substantially different. It shares characteristics with patented Philodendron plant varieties 'Prince of Orange' (U.S. Plant Pat. No.: 6,797, Miller, May 16, 1989); 'Black Cardinal' (U.S. Plant Pat. No.: 5,355, McColley, Nov. 20, 1984); and 'Royal King' (U.S. Plant Pat. No.: 3,831, McColley, Mar. 2, 1976). Comparison with these three varieties highlights the distinctive combination of characteristics to be found in Philodendron 'McColley's Finale'.

'Prince of Orange': This is a self-heading variety in which the new leaves are bright, glossy orange maturing to yellow-green. The leaves have an ovate shape with the tip acute and the base hastate. In comparison, my new variety has bright chestnut red color in the new leaves, which mature to a medium green with dark chestnut red shading over the surface. The leaves are similar in shape, but with the leaf base on my new variety being more cordate. To the casual observer, my new variety gives the impression of being a red color version of 'Prince of Orange'. There is undoubtedly a substantial degree of shared parentage, but the two are quite distinctive from one another.

'Black Cardinal': This is a self-heading variety in which the new leaves are brick red and mature to black red. The leaves have an elliptic shape with a distinctly undulate surface, cuspidate leaf tip and sagittate base. In comparison, my new variety is wholly different except for also being self-heading and there being slight similarity in coloration of the newest leaves. In 'Black Cardinal', the brick red color of the newest leaves quickly darkens to near black as the leaf matures, and the leaves remain dark. In my new variety, the red color of the newest leaves is much brighter, darkens to a deep chestnut red as the leaf matures, and then fades to a medium green leaf color burnished with dark chestnut red.

'Royal King': This is a vining variety in which the leaves are shades of yellow-green and the leaves have a narrowly ovate shape with the tip acute and the base cordate. In comparison, my new variety is entirely different except for some similarity in the shape of the leaves. In the early stages of growth of 'Royal King', before the vining habit becomes obvious, the casual observer may have a first impression that my new variety is a deeply colored version of 'Royal King', largely due to similarity of deportment of the leaves in immature plants of 'Royal King'. This impression does not withstand close inspection of the plants and does not exist in comparing mature plants.

Philodendron 'McColley's Finale' is highly colorful. The new leaves are a glossy, rich chestnut red (Munsell Limit Color Cascade 36-13), and as the leaves mature, they initially darken to a deeper shade of chestnut red (36-14, 36-15), and with increasing maturity the leaf color fades to reveal medium green (22-14) leaves stained with dark red. The dark chestnut red petioles add to the overall colorful impact of the plant. The plant is a compact rosette with thick petioles arising in a whorl from a crown or short stalk. At maturity, the shape of the leaves is ovate. Pinnate venation with large flattened midribs are notable, as are the thick, leathery, glossy, colorful leaves. The width of the leaf is approximately two-thirds the length.

The petioles are erect to semi-erect, approximately 7–8 inches long, and are black red tinged with purple (40-16) in color, remaining darkly colored at maturity. The internodes are one-half inch or less. Cataphylls are dark chestnut red (36-15, 36-16) in color.

Since my new variety is a true rosette and essentially without a stem, it is compact. Growth is uniform and of good substance. Under good growing conditions, medium light intensity, moderate to high humidity and moderate temperatures, growth is fast, but without the plant becoming leggy. With high humidity and warm temperature (85° F. or higher), one leaf per week is produced, resulting in a plant 18 inches–24 inches in diameter within 6 months of planting. The rich chestnut red color is maintained in rapid growth periods.

The typical commercial-sized plant for a five-inch pot is approximately eleven inches-twelve inches tall (measured from soil surface), with the rosette having a diameter of approximately twenty-two inches. The typical commercial-sized plant for a ten-inch pot is approximately fifteen inches-sixteen inches tall (measured from soil surface), with the rosette having a diameter of 36 inches.

The growth of the plant indoors is good. It tolerates air-conditioning, infrequent watering, and a lack of fertilization. If provided with adequate light, it retains its form and color indoors. The plant performs best with regular care, but over-watering is detrimental.

This new variety is resistant to bacterial leaf rot and fungal leaf spot. In the same growing facilities, it is hardier than Philodendron 'Prince of Orange'.

BRIEF DESCRIPTION OF THE DRAWINGS

The accompanying photographs clearly depict the new variety.

DETAILED DESCRIPTION

Figure 1:
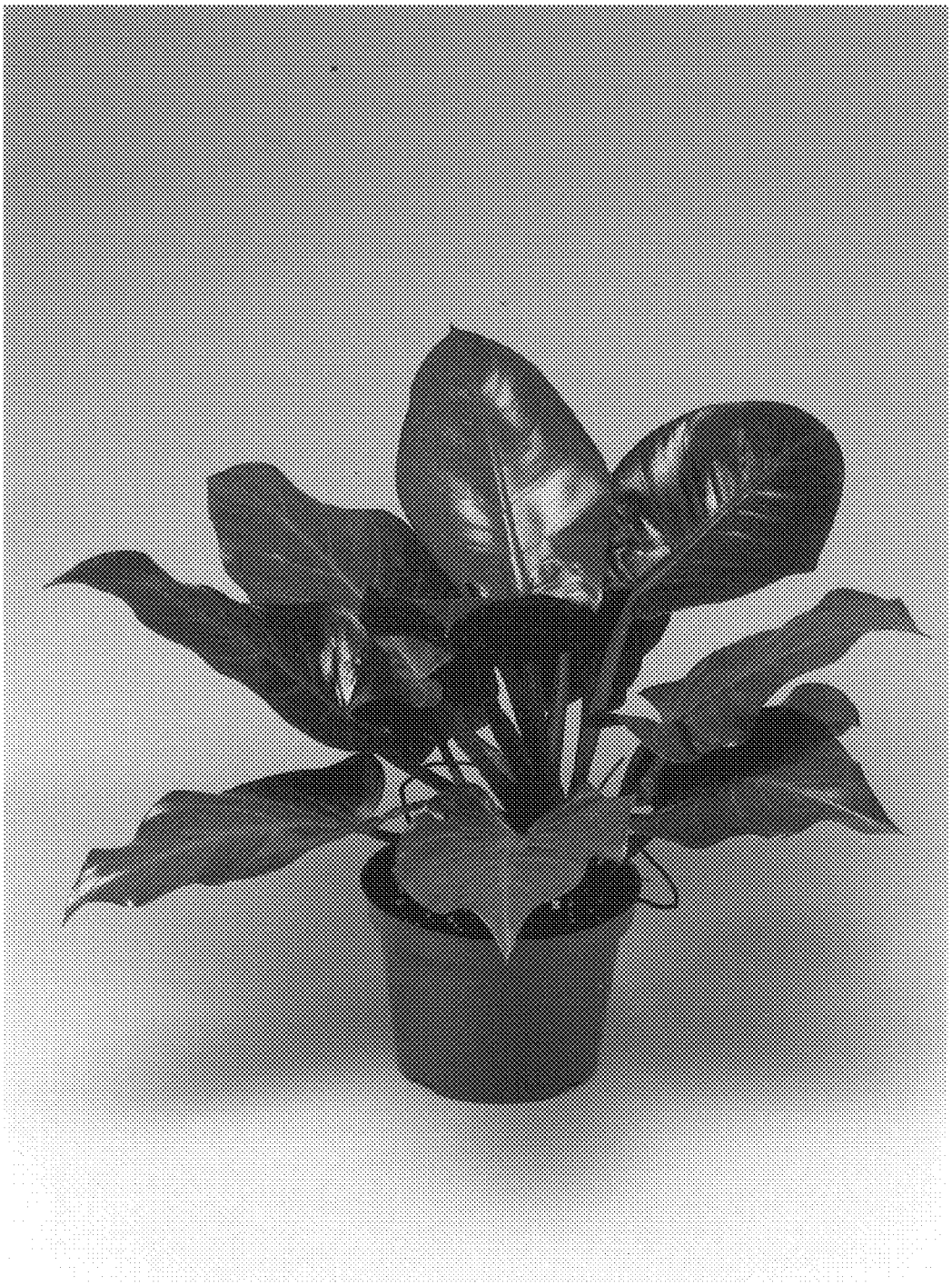
FIG. 1: shows Philodendron 'McColley's Finale' from a side perspective, disclosing the overall appearance, growth habit and coloration.
Figure 2:
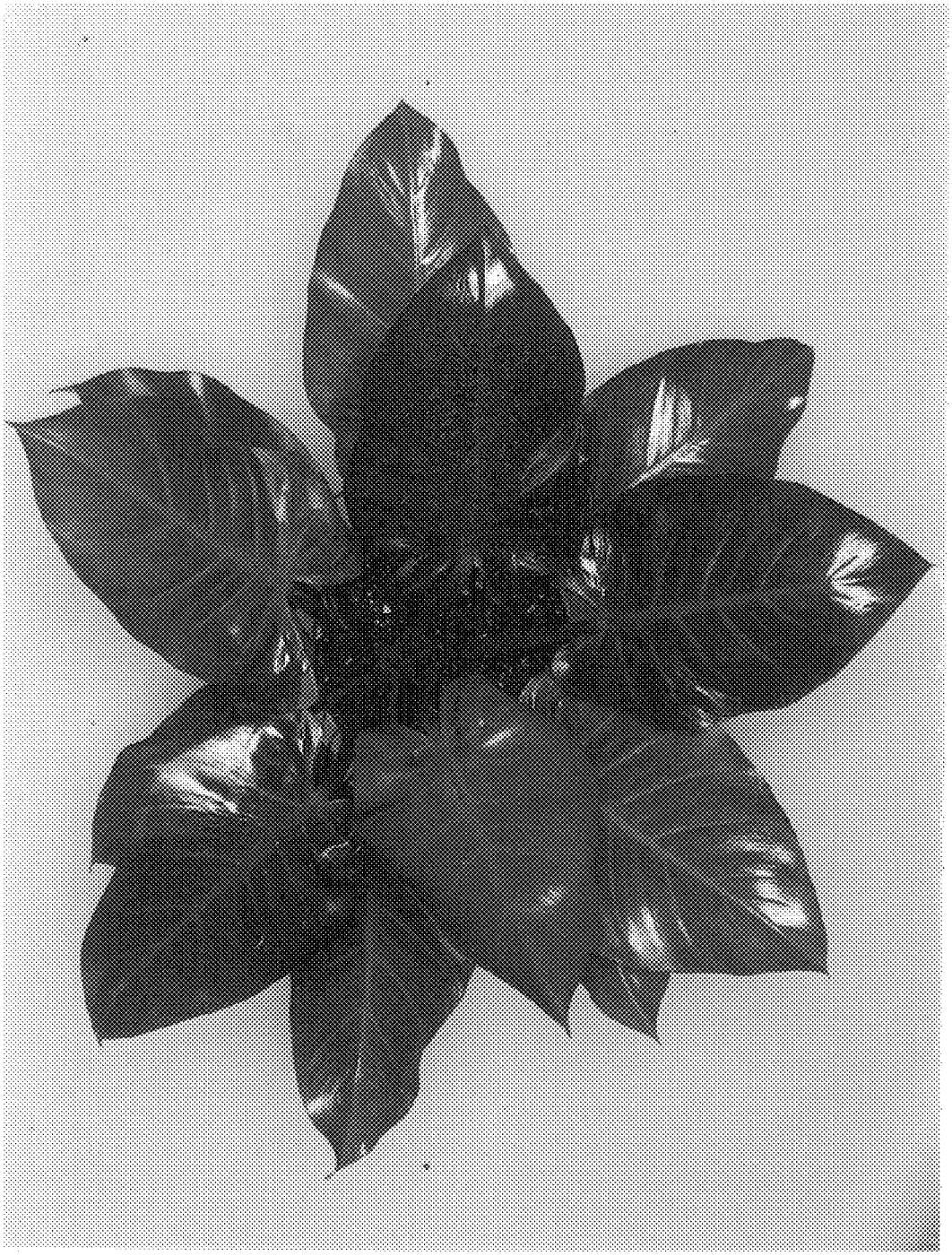
FIG. 2: shows Philodendron 'McColley's Finale' from above, disclosing the rosette shape and the overall appearance of the plant, including coloration, from the vantage at which it would normally be viewed when used for interior landscaping.

The following is a detailed description of my new variety, based on observations of mature specimens (approximate 36-inch diameter rosette) grown one year following potting of crown offshoot cutting in the vicinity of Orlando, Fla. in greenhouse conditions. Ambient temperature typically ranged between 60° F. and 90° F., increasing to 95° F. for short periods during the hot summer months. Natural sunlight intensity was controlled by use of shadecloth and shading compounds to reduce light intensity to approximately 1500–1800 footcandles. Irrigation occurred as needed to maintain moist potting media, with fertilizer in a 3-1-2 ratio being applied in solution at a rate of 400–600 pounds of nitrogen per acre per year. Color references are made to the Munsell Limit Color Cascade published by Macbeth Color & Photometry Division of Kollmorgen Company.

I. Parentage: Unknown complex hybrid.

II. Propagation: Holds its distinguishing characteristics through succeeding generations of asexually reproduced plants. Successful reproduction has been accomplished by removal of crown offshoots and by organogenesis tissue culture propagation utilizing meristematic explants.

III. Form: The plant forms a rosette, normally having a diameter at least twice the height of the plant. At maturity the height is approximately 15 inches to 16 inches, with a 36 inch diameter rosette.

IV. Growth: A moderately fast-growing plant compared to other self-heading varieties of Philodendron. The growth rate of my new variety is similar to Philodendron 'Prince of Orange'. A mature 36 inch diameter rosette is formed from a liner-sized plant in approximately one year.

V. Blooming habit: My new variety has been brought to flower during the course of several years of experimental growing. It has a typical Philodendron inflorescence of no commercial significance. The inflorescence is composed of a spathe which surrounds a spadix. The spadix is approximately 3 inches long with male flowers superior to female flowers on the spadix, and with a sterile band separating male and female flowers. Individual flowers are inconspicuous, 1–2 mm in diameter or less, with no noticeable calyx or corolla to the unaided eye, and number approximately 400–800 per inflorescence. The spathe is closely proximate to the stem, such that the inflorescence is held below the level of the foliage, and is dark chestnut red (36-15, 36-16) in color, maturing to medium green (22-14) tinged with dark chestnut red (36-15). The spathes remain attached for four months or longer. No setting of seed has been observed.

VI. Foliage:

*A. Leaf shape.*—a. Mature — ovate. b. Immature — ovate. c. Tip — acute. d. Base — imperfectly cordate. e. Displacement — smooth to undulate. f. Margin — entire. g. Venation — pinnate.

*B. Leaf attachment.*—Petiolate; internodes along plant stalk one-half inch or less.

*C. Leaf arrangement.*—Alternate.

*D. Leaf size.*—14–16 inches long and 7.5–8.5 inches wide at the widest point.

*E. Petiole.*—Length is 7–8 inches; erect to semi-erect; one-half inch in diameter; round with flat slightly concaved upper surface.

*F. Cataphylls.*—Persistent; 5–7 inches long.

*G. Color characteristics.*—a. Mature Leaf: 1. Top and Bottom Surface — medium green (22–14) tinged with dark chestnut red (36-14 to 36-15). b. Immature Leaf: 1. Top and Bottom Surface — bright chestnut red (36-13). c. Leaf Venation: 1. Midrib — immature — same as leaf surface color; mature — yellow-green (24-12). 2. Veins — immature — same as leaf surface color; mature — yellow-green (24-12). d. Petiole — black-red slightly tinged with purple (40-16). e. Cataphyll — dark chestnut red (36-15, 36-16).

I claim:

1. A new and distinct variety of Philodendron plant, as herein illustrated and described.

* * * * *